United States Patent
Imamura et al.

(10) Patent No.: US 8,216,145 B2
(45) Date of Patent: Jul. 10, 2012

(54) ULTRASONIC DIAGONSTIC APPARATUS, ULTRASONIC IMAGE PROCESSING APPARATUS, AND ULTRASONIC IMAGE PROCESSING METHOD

(75) Inventors: Tomohisa Imamura, Nasushiobara (JP); Koichiro Kurita, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 630 days.

(21) Appl. No.: 12/338,101

(22) Filed: Dec. 18, 2008

(65) Prior Publication Data
US 2009/0171207 A1 Jul. 2, 2009

(30) Foreign Application Priority Data
Dec. 26, 2007 (JP) ................. 2007-335336

(51) Int. Cl.
*A61B 8/00* (2006.01)
*G06K 9/00* (2006.01)
(52) U.S. Cl. .............. 600/443; 600/437; 382/128
(58) Field of Classification Search .............. 600/437, 600/443–449; 382/128
See application file for complete search history.

(56) References Cited

U.S. PATENT DOCUMENTS
2006/0020205 A1* 1/2006 Kamiyama ............. 600/437
2007/0065009 A1* 3/2007 Ni et al. ................. 382/173

FOREIGN PATENT DOCUMENTS
CN 1718164 A 1/2006
CN 1919144 A 2/2007

* cited by examiner

*Primary Examiner* — Michael Rozanski
(74) *Attorney, Agent, or Firm* — Oblon, Spivak, McClelland, Maier & Neustadt, L.L.P.

(57) ABSTRACT

Low-resolution image data for recognizing signal components macroscopically is generated, an effective diagnostic component and an ineffective diagnostic component are determined by using the low-resolution image data, and a correction coefficient is decided for every pixel such that the correction coefficient is set to 1 for the effective diagnostic component and the correction coefficient is set to equal to or larger than 0 and smaller than 1 for the ineffective diagnostic component. In addition, correction processing for raising the contrast between the effective diagnostic component and the ineffective diagnostic component by multiplying each pixel value of original image data by a corresponding correction coefficient is executed.

18 Claims, 6 Drawing Sheets

ULTRASONIC DIAGONSTIC APPARATUS, ULTRASONIC IMAGE PROCESSING APPARATUS, AND ULTRASONIC IMAGE PROCESSING METHOD

CROSS-REFERENCE TO RELATED APPLICATIONS

This application is based upon and claims the benefit of priority from prior Japanese Patent Application No. 2007-335336, filed Dec. 26, 2007, the entire contents of which are incorporated herein by reference.

BACKGROUND OF THE INVENTION

1. Field of the Invention

The present invention relates to an ultrasonic diagnostic apparatus, an ultrasonic image processing apparatus, and an ultrasonic image processing method of performing filtering processing for further emphasizing the contrast between a signal component from a tissue or the like and a noise component.

2. Description of the Related Art

The ultrasonic diagnosis makes it possible that the pulsation of the heart or the movement of an embryo is displayed in real time by a simple operation of bringing an ultrasonic probe into contact with a body surface. In addition, since the ultrasonic diagnosis is very safe, the test may be repeatedly performed. In addition, the system size is small compared with other diagnostic apparatuses, such as an X ray, a CT, and an MRI, and a test at the bedside can also be easily performed. For this reason, it can be said that the ultrasonic diagnosis is an easy diagnostic method. An ultrasonic diagnostic apparatus used in the ultrasonic diagnosis changes in various ways with the type of a function that the ultrasonic diagnostic apparatus has. As a small ultrasonic diagnostic apparatus, an ultrasonic diagnostic apparatus that is so small as to be carried with one hand is being developed. In addition, since the ultrasonic diagnosis does not cause radioactive exposure unlike the X ray, the ultrasonic diagnosis may also be used in an obstetric treatment, a remote medical treatment, and the like.

However, when performing diagnostic imaging using an ultrasonic image acquired by such an ultrasonic diagnostic apparatus, a signal component from a tissue and a noise component may not be easily distinguished from each other. In this case, it is common to reduce the noise component by performing predetermined filtering processing.

However, when reducing a noise component using a known method, sometimes, a signal component from a tissue or the blood flow is also reduced simultaneously and the contrast between the signal component from the tissue and the like and the noise component is not sufficient.

BRIEF SUMMARY OF THE INVENTION

In view of the above, it is an object of the present invention to provide an ultrasonic diagnostic apparatus, an ultrasonic image processing apparatus, and an ultrasonic image processing method capable of raising the visibility by improving the contrast between a signal component corresponding to a tissue and the like and a signal component corresponding to a noise.

According to an aspect of the present invention, there is provided an ultrasonic diagnostic apparatus including: a data generating unit that transmits an ultrasonic wave to a predetermined region of a tested body and generates first ultrasonic image data on the basis of a reflected wave from the tested body; a determination unit that generates second ultrasonic image data, the resolution of which is lower than that of the first ultrasonic image data, using the first ultrasonic image data and determines an effective diagnostic component and an ineffective diagnostic component on the basis of the second ultrasonic image data; a coefficient deciding unit that decides correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and a multiplication unit that executes image correction processing by multiplying the ineffective diagnostic component and the effective diagnostic component of the first ultrasonic image data by the correction coefficients.

According to another aspect of the present invention, there is provided an ultrasonic image processing apparatus including: a storage unit that transmits an ultrasonic wave to a predetermined region of a tested body and stores first ultrasonic image data generated on the basis of a reflected wave from the tested body; a determination unit that generates second ultrasonic image data, the resolution of which is lower than that of the first ultrasonic image data, using the first ultrasonic image data and determines an effective diagnostic component and an ineffective diagnostic component on the basis of the second ultrasonic image data; a coefficient deciding unit that decides correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and a multiplication unit that executes image correction processing by multiplying the ineffective diagnostic component and the effective diagnostic component of the first ultrasonic image data by the correction coefficients.

According to yet another aspect of the present invention, there is provided an ultrasonic image processing method including: transmitting an ultrasonic wave to a predetermined region of a tested body and generating second ultrasonic image data, the resolution of which is lower than that of the first ultrasonic image data, using the first ultrasonic image data generated on the basis of a reflected wave from the tested body; determining an effective diagnostic component and an ineffective diagnostic component on the basis of the second ultrasonic image data; deciding correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and executing image correction processing by multiplying the ineffective diagnostic component and the effective diagnostic component of the first ultrasonic image data by the correction coefficients.

DETAILED DESCRIPTION OF THE INVENTION

Figure 1:
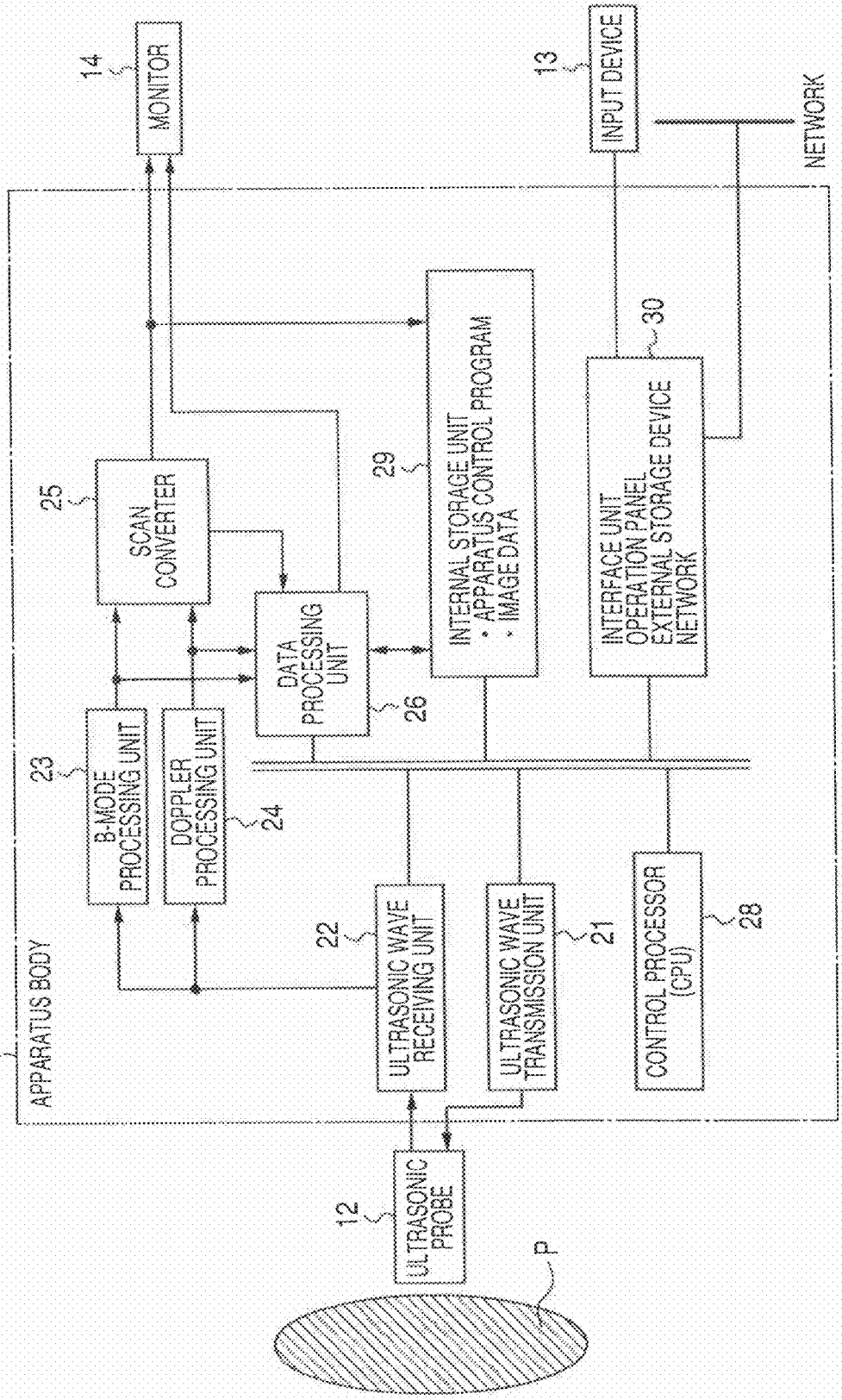
FIG. 1 is a block diagram illustrating the configuration of an ultrasonic diagnostic apparatus according to an embodiment.

Hereinafter, an embodiment of the present invention will be described with reference to the accompanying drawings. Moreover, in the following description, components having approximately the same function and configuration are denoted by the same reference numeral, and a repeated explanation thereof will only be made as needed.

FIG. 1 is a block diagram illustrating the configuration of an ultrasonic diagnostic apparatus 1 according to the present embodiment. As shown in the drawing, the ultrasonic diagnostic apparatus 1 includes an ultrasonic probe 12, an input device 13, a monitor 14, an ultrasonic wave transmission unit 21, an ultrasonic wave receiving unit 22, a B-mode processing unit 23, a Doppler processing unit 24, a scan converter 25, a data processing unit 26, a control processor (CPU) 28, an internal storage unit 29, and an interface unit 30. Hereinafter, functions of the constituent components will be described.

The ultrasonic probe 12 generates an ultrasonic wave on the basis of a driving signal from the ultrasonic wave transmission unit 21 and has a plurality of piezoelectric vibrators that convert a reflected wave from a tested body into an electric signal, a matching layer provided in the piezoelectric vibrators, a backing material that prevents propagation of an ultrasonic wave rearward from the piezoelectric vibrators, and the like. When ultrasonic waves are transmitted from the ultrasonic probe 12 to a tested body P, the transmitted ultrasonic waves are sequentially reflected on a discontinuous surface of acoustic impedances of body tissues and are then received as an echo signal by the ultrasonic probe 12. The amplitude of the echo signal depends on a difference of acoustic impedances on the discontinuous surfaces on which the ultrasonic waves are reflected. In addition, an echo generated when transmitted ultrasonic pulses are reflected from a moving blood flow, a heart wall, and the like receives frequency shift depending on a speed component of a moving body in the ultrasonic wave transmission direction by the Doppler effect.

The input device 13 is connected to an apparatus body 11 and has various switches, buttons, a track ball, a mouse, a keyboard, and the like used to input various kinds of instructions from an operator, an instruction for setting a condition or a region of interest (ROI), an instruction for setting various image quality conditions, and the like on the apparatus body 11. For example, when a user operates a stop button or a FREEZE button of the input device 13, transmission and reception of an ultrasonic wave are stopped and the ultrasonic diagnostic apparatus is temporarily stopped.

The monitor 14 displays morphological information or blood flow information of a body on the basis of a video signal from the scan converter 25.

The ultrasonic wave transmission unit 21 has a trigger generating circuit, a delay circuit, and a pulse circuit which are not shown. The pulse circuit repeatedly generates a rate pulse for forming a transmitted ultrasonic wave at a predetermined rate frequency fr Hz (period; 1/fr second). In addition, the delay circuit gives a delay time, which is required for making ultrasonic waves converge in the beam shape for every channel and for determining transmission directivity, to each rate pulse. The trigger generating circuit applies a driving pulse to the probe 12 at the timing based on the rate pulse.

In addition, the ultrasonic wave transmission unit 21 has a function of changing a transmission frequency, a transmitted driving voltage, and the like instantaneously in order to execute a predetermined scan sequence according to the instruction of the control processor 28. In particular, the change of the transmitted driving voltage is realized by a linear amplifier type signal transmission circuit capable of changing the value instantaneously or a mechanism which performs electric switching of a plurality of power supply units.

The ultrasonic wave receiving unit 22 has an amplifying circuit, an A/D converter, an adder, and the like which are not shown. The amplifying circuit amplifies an echo signal received through the probe 12 for every channel. The A/D converter gives a delay time, which is required to determine the receiving directivity, to the amplified echo signal, and then the adder performs adding processing. By this addition, a reflected component from a direction according to the receiving directivity of echo signals is emphasized and overall beams in ultrasonic transmission and reception are formed by the receiving directivity and the transmission directivity.

The B-mode processing unit 23 receives an echo signal from the ultrasonic wave receiving unit 22, performs logarithmic amplification and envelope detection processing, and generates data in which the signal strength is expressed as brightness. This data is transmitted to the scan converter 25 and is displayed on the monitor 14 as a B-mode image which expresses the strength of a reflected wave with the brightness.

The Doppler processing unit 24 makes a frequency analysis of speed information from the echo signal received from the ultrasonic wave receiving unit 22, extracts echo components due to the Doppler effect for a blood flow, a tissue or a contrast agent, and calculates blood flow information, such as an average speed, diffusion, and power, with respect to multiple points. The acquired blood flow information is transmitted to the scan converter 25 to be color-displayed on the monitor 14 as an average speed image, a diffusion image, a power image, and a combination image thereof.

The scan converter 25 mixes an ultrasonic scanning line signal of data received from the B-mode processing unit 23, the Doppler processing unit 24, and the data processing unit 26 with character information, scale, and the like of various parameters converts the result into a scanning line signal row in a typical video format represented by a television, and generates an ultrasonic diagnostic image as a display image. The scan converter 25 has a storage memory in which image data is stored, for example, so that an operator can call an image recorded in a test after diagnosis. In addition, data before being input to the scan converter 25 is, for example, a group of amplitude values or brightness values for every spatial position and is called 'raw data'.

The data processing unit 26 executes processing according to an ineffective diagnostic component reduction function, which will be described later, on the basis of the control from the control processor 28 using raw data before scan conversion or image data after scan conversion.

The control processor 28 has a function as an information processing device (computer), and is a control unit that controls an operation of the ultrasonic diagnostic apparatus body. The control processor 28 reads from the internal storage unit 29 a control program for executing image generation, image display, and the like, loads the control program onto the memory that the control processor 28 has, and executes calculation, control, and the like on various kinds of processing.

The internal storage unit 29 stores a control program for executing image generation and display processing and scan sequence to be described later, diagnostic information (for example, a patient ID and doctor's opinion), a diagnostic protocol, transmission and reception conditions, a CFAR processing control program, a body mark generating program, and other data groups. Moreover, the internal storage unit 29 may also be used to store an image in the image memory 26 as needed. The data in the internal storage unit 29 may also be transmitted to an external peripheral device through the interface circuit 30.

The interface unit 30 is an interface related to the input device 13, a network, and a new external storage device (not shown). Data or an analysis result of an ultrasonic image obtained by the apparatus may be transmitted to other apparatuses through the network by the interface unit 30.

(Ineffective Diagnostic Component Reduction Function)

Next, an ineffective diagnostic component reduction function that the ultrasonic diagnostic apparatus 1 has will be described. This function is to reduce an ineffective diagnostic component included in an echo signal such that the contrast between a signal component (for example, a signal component from a region which is effective for diagnosis and is called a blood flow or a tissue; referred to as an 'effective diagnostic component') which contributes as information effective for diagnosis and a signal component (for example, a noise component; referred to as an 'ineffective diagnostic component') which does not contribute as information effective for diagnosis is further emphasized in an ultrasonic image. Since this function enables, for example, the contrast between the brightness corresponding to a tissue region contributing as information effective for diagnosis and the brightness corresponding to a noise portion not contributing as information effective for diagnosis to be emphasized on a display image, the visibility of an ultrasonic image can be improved.

Moreover, in the present embodiment, for the purpose of specific explanation, a case where the ineffective diagnostic component reduction function is applied to image data, which is the data after scan conversion, will be exemplified. However, the function may also be applied to raw data which is data before scan conversion regardless of a data format.

Moreover, in the present embodiment, a case where the ultrasonic diagnostic apparatus 1 executes the ineffective diagnostic component reduction function will be described as an example. However, a function of imaging an ultrasonic image is not essential in realizing the ineffective diagnostic component reduction function. For example, it may be possible to install a dedicated program in an ultrasonic image processing apparatus, such as a medical workstation, and to execute the ineffective diagnostic component reduction processing on ultrasonic image data which is raw data acquired beforehand.

Moreover, in the present embodiment, for the purpose of specific explanation, a case where the ineffective diagnostic component reduction function is applied to ultrasonic image data acquired by B-mode imaging will be exemplified. However, the function may also be applied to ultrasonic image data acquired in other image modes, such as a Doppler mode, regardless of an imaging mode.

Figure 2:
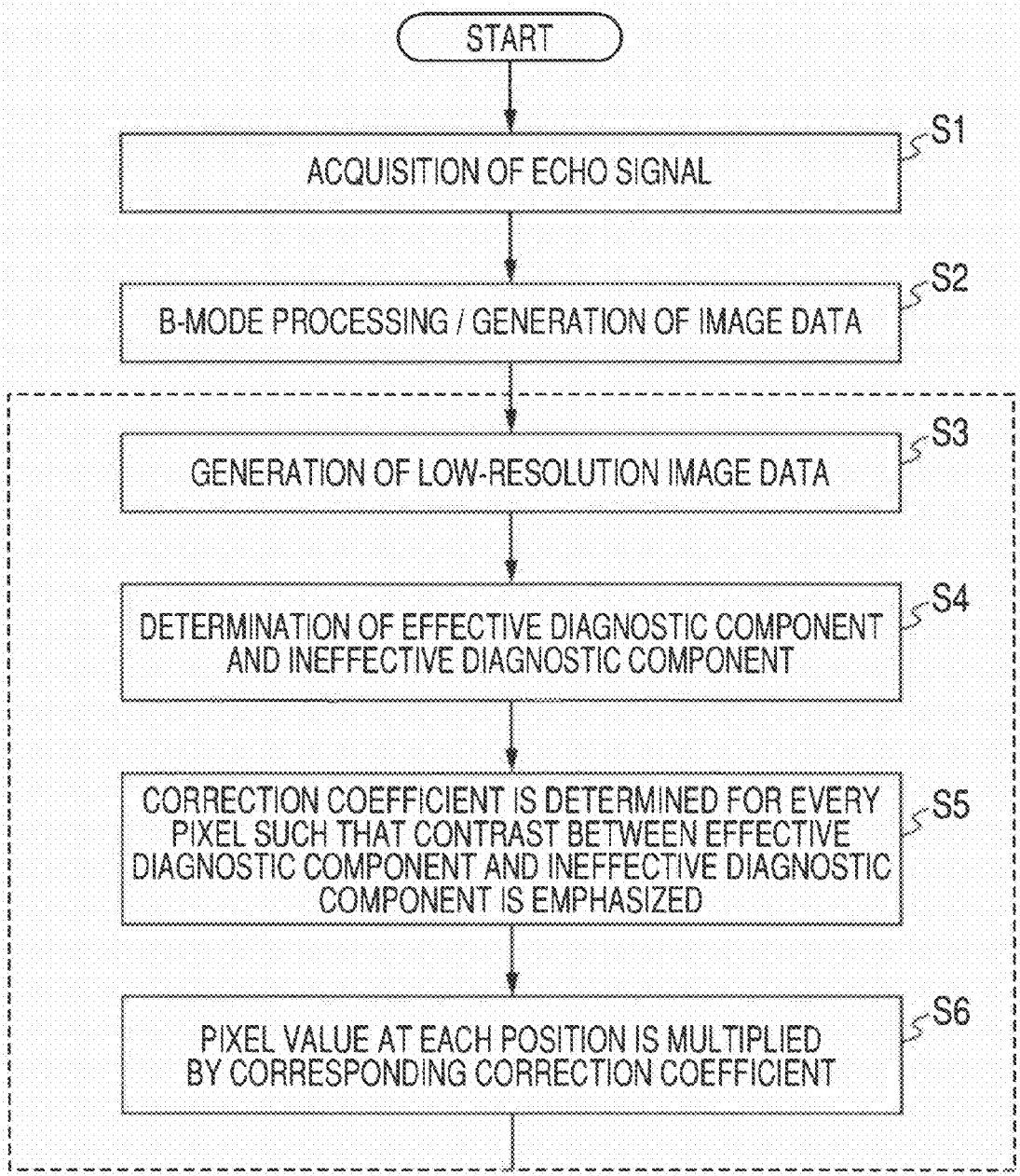
FIG. 2 is a flow chart illustrating the flow of ineffective diagnostic component reduction processing.

FIG. 2 is a flow chart illustrating the flow of ineffective diagnostic component reduction processing. Hereinafter, the content of the processing in each step will be described. In this flow chart, steps S3 to S6 correspond to the ineffective diagnostic component reduction processing.

[Ultrasonic Scan (Acquisition of an Echo Signal): Step S1]

First, the control processor 28 executes B-mode imaging according to a predetermined scan sequence and acquires an echo signal (step S1).

[B-Mode Processing (Generation of Image Data): Step S2]

Next, the B-mode processing unit 23 performs logarithmic amplification and envelope detection processing on the acquired echo signal and generates raw data. The scan converter 25 generates image data using the raw data received from the B-mode processing unit 23 (step S2).

[Generation of Low-Resolution Image Data: Step S3]

Then, the data processing unit 26 generates low-resolution image data using a predetermined method (step S3). Here, the low-resolution image data is smoothed image data generated by using the image data acquired in step S2 in order to lower the resolution compared with an original image.

The low-resolution image data distinguishes a tissue component from a non-tissue component by recognizing signals macroscopically. Although the generation method is not limited, typical examples thereof include filtering processing using a blur filter and the following methods, for example. That is, first, mapping processing of setting a small region (for example, a small region of 3×3=9 pixels) with a predetermined size on image data, calculating an average value of the small region using a predetermined window function, and setting the average value as a value of a pixel corresponding to a middle position of the small region is performed. Then, the middle of the small region is moved to an adjacent pixel, for example, to perform the same mapping processing. By executing such mapping processing on all pixels on the image data, the low-resolution image data can be generated. In addition, as another method, the low-resolution image data may be generated by thinning out image data output from the scan converter 25 in a predetermined rate (for example, ½ or ⅓) and then making the size return to the original size using predetermined interpolation processing.

[Determination of Effective Diagnostic Component and Ineffective Diagnostic Component (Generation of a Quantized Image): Step S4]

Figure 3:
FIG. 3 is a view illustrating an example of a quantized image obtained by determination processing on a boundary of an effective diagnostic component and an ineffective diagnostic component.

Then, the data processing unit 26 determines an effective diagnostic component and an ineffective diagnostic component using the low-resolution image data and generates a quantized image in which the effective diagnostic component is set to 1 and the ineffective diagnostic component is set to 0 as shown in FIG. 3, for example (step S4). The determination method is not particularly limited. Typical examples of the determination method may include: determination using multiplication processing (integration processing) of a predetermined function or coefficient or threshold processing based on the distribution of a pixel value of the low-resolution image data; determination using threshold processing based on the change rate (differential coefficient) of a pixel value of the low-resolution image data; and the like.

[Correction Coefficient Decision of Effective Diagnostic Component and Ineffective Diagnostic Component: Step S5]

Next, the data processing unit 26 decides a correction coefficient for every pixel by using the boundary between the low-resolution image data and the effective diagnostic component and the ineffective diagnostic component (step S5). For example, when a pixel value (gradation)=80 is determined to the boundary between the effective diagnostic component and the ineffective diagnostic component in step S4 in the case of 128 gradation levels, the data processing unit 26 decides a correction coefficient of the low-resolution image data for every pixel on the basis of the correspondence relationship set beforehand as shown in FIG. 4, for example, such that a coefficient equal to or larger than 0 and smaller than 1 is assigned for a pixel (pixel having a value equal to or larger than 0 and smaller than 80) corresponding to the ineffective diagnostic component and a coefficient 1 is assigned for a pixel (pixel having a value equal to or larger than 80 and smaller than 128) corresponding to the effective diagnostic component.

Figure 4:
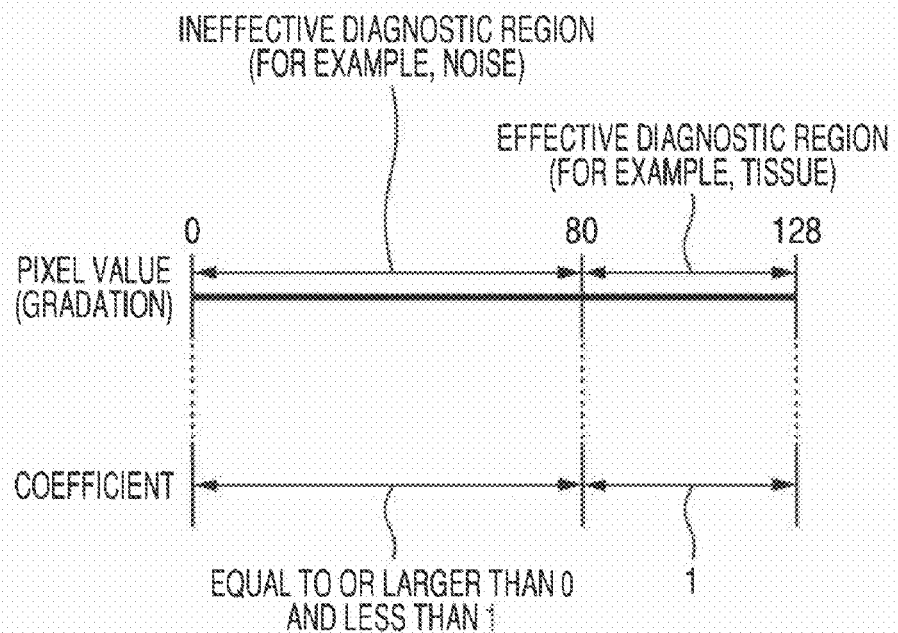
FIG. 4 is a view explaining an example of correction coefficient decision processing for an effective diagnostic component and an ineffective diagnostic component.

In addition, a method for the coefficient decision in this step is not limited to an example shown in FIG. 4. For example, a coefficient may also be decided by using predetermined computation expression, correspondence table, and the like stored beforehand in the internal storage unit 29.

[Signal Value after Positioning is Multiplied by a Corresponding Correction Coefficient: Step S6]

Then, the data processing unit 26 multiplies each pixel value of original image data acquired in step S2 by a corresponding correction coefficient and executes correction processing for raising the contrast between the effective diagnostic component and the ineffective diagnostic component (step S6).

[Display of an Ultrasonic Image: Step S7]

Then, the monitor 14 displays the ultrasonic image, in which the contrast between the effective diagnostic component and the ineffective diagnostic component is emphasized, in a predetermined format on the basis of a video signal from the data processing unit 26 (step S7).

Figure 5:
FIG. 5 is a view illustrating an ultrasonic image on which ineffective diagnostic component reduction processing was executed and in which the contrast between an effective diagnostic component and an ineffective diagnostic component is emphasized.
Figure 6:
FIG. 6 is a view illustrating a normal ultrasonic image on which the ineffective diagnostic component reduction processing was not executed.

FIG. 5 is a view illustrating an ultrasonic image on which the ineffective diagnostic component reduction processing was executed. FIG. 6 is a view illustrating a normal ultrasonic image on which the ineffective diagnostic component reduction processing was not executed.

Comparing FIGS. 5 and 6, it can be seen that in the case of FIG. 5, the contrast between the effective diagnostic component and the ineffective diagnostic component is further emphasized by the ineffective diagnostic component reduction processing, compared with FIG. 6.

(Data Amount Reduction Function)

Next, a data amount reduction function of the ultrasonic diagnostic apparatus will be described. This function is to rotate ultrasonic image data for every frame and to reduce the total amount of data written into a memory/the total amount of data read from a memory. By executing processing (data amount reduction processing) based on the function, for example, before the ineffective diagnostic component reduction processing, the throughput until the ultrasonic image is displayed can be improved and the ultrasonic image display can be realized in real time.

Figure 7A:
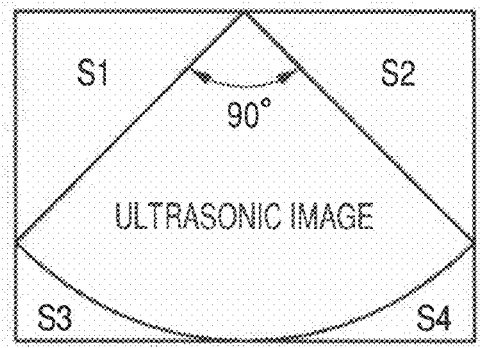
FIGS. 7A, 7B, and 7C are views illustrating an example for explaining the data amount reduction processing.
Figure 7B:
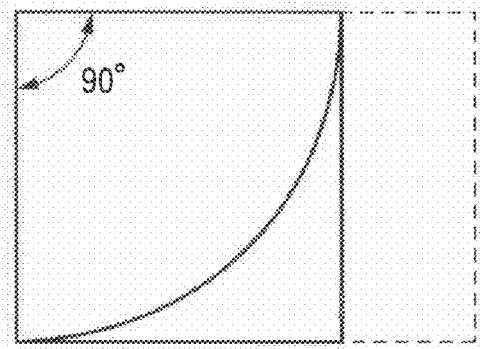
Figure 7C:
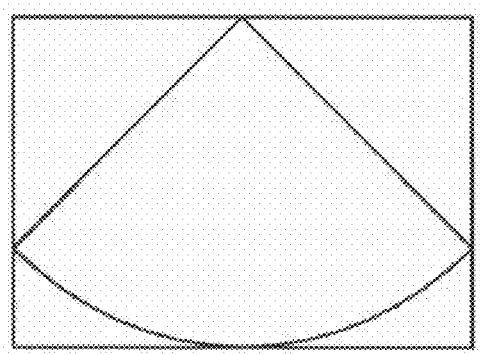

FIGS. 7A, 7B, and 7C are views illustrating an example for explaining the data amount reduction processing. When ultrasound scan based on sector scan is performed, image data after scan conversion has a fan shape shown in FIG. 7A. When writing/reading the image data with the fan shape into a memory, the image data is written into and read from a rectangular region shown in FIG. 7A in a known apparatus. For this reason, the writing/reading was also performed in unnecessary regions, such as S1, S2, and S3, other than ultrasonic image data.

In this data amount reduction processing, for example, the data processing unit 26 rotates the obtained ultrasonic image data on the basis of the shape or size of an ultrasonic scan region such that the area of a rectangular region including the image data becomes minimal as shown in FIG. 7B, thereby minimizing a memory region used to write/read the image data. The above-described ineffective diagnostic component reduction processing is executed on the image data written in the memory region minimized as described above. Then, the image data is rotated to return to the original direction, as shown in FIG. 7C. Thus, it is possible to reduce the total amount of data written into the memory/total amount of data read from the memory and to improve the throughput until the ultrasonic image is displayed. As a result, the ultrasonic image display can be realized in real time.

Figure 8A:
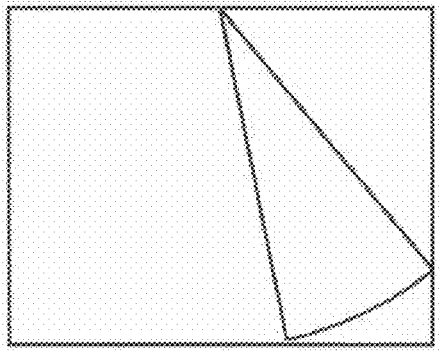
FIGS. 8A, 8B, and 8C are views illustrating another example for explaining the data amount reduction processing.
Figure 8B:
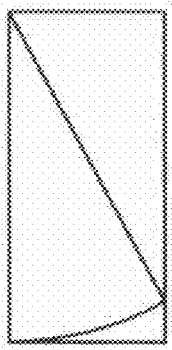
Figure 8C:
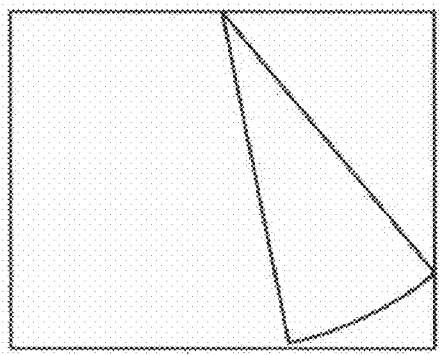

Furthermore, also when an ultrasonic scan region is inclined with respect to an ultrasonic wave irradiation surface as shown in FIG. 8A, for example, image data is rotated such that the area of a rectangular region including the image data becomes minimal as shown in FIG. 8B, thereby minimizing a memory region used to write/read the image data. Then, after executing the above-described ineffective diagnostic component reduction processing, the image data is rotated to return to the original direction, as shown in FIG. 8C. Thus, the throughput until the ultrasonic image is displayed can be improved, and the ultrasonic image display can be realized in real time.

According to the configuration described above, the following effects can be obtained.

In the ultrasonic diagnostic apparatus according to the present embodiment, low-resolution image data for recognizing signal components macroscopically is generated, an effective diagnostic component and an ineffective diagnostic component are determined by using the low-resolution image data, and a correction coefficient is decided for every pixel such that the correction coefficient is set to 1 for the effective diagnostic component and the correction coefficient is set to be equal to or larger than 0 and smaller than 1 for the ineffective diagnostic component. In addition, each pixel value of original image data is multiplied by a corresponding correction coefficient and the correction processing for raising the contrast between the effective diagnostic component and the ineffective diagnostic component is executed. That is, since a correction coefficient 1 is set for the effective diagnostic component, the image quality of the corresponding region is maintained. On the other hand, since a correction coefficient equal to or larger than 0 and smaller than 1 is set for the ineffective diagnostic component, the ineffective diagnostic component is corrected such that the pixel value is further lowered. Accordingly, the contrast between the effective diagnostic component and the ineffective diagnostic component can be emphasized while maintaining the image quality of the effective diagnostic component. As a result, the contrast between a signal component corresponding to the tissue or the like and a signal component corresponding to a noise can be improved to thereby improve the visibility, which contributes to reducing the load in an observation work in diagnostic imaging and improving the quality of the diagnostic imaging.

Furthermore, in the ultrasonic diagnostic apparatus, when writing image data into a memory, the amount of data to be processed can be reduced by rotating the ultrasonic scan range such that the amount of data written or read becomes minimal. As a result, the throughput until the ultrasonic image is displayed can be improved, and the ultrasonic image display can be realized in real time.

In addition, the present invention is not limited to the embodiment described above but may be embodied in practice by modifying constituent components without departing from the scope and spirit of the present invention. For example, specific modifications include the following examples.

(1) Each of the functions in the present embodiment may be realized by installing a program, which is used to execute corresponding processing, in a computer, such as a workstation, and loading the program onto a memory. In this case, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

(2) In the above embodiment, a correction coefficient 1 is set for a pixel of a corresponding region in order to maintain the image quality of an effective diagnostic component. However, one object of the ineffective diagnostic component reduction processing is to raise the contrast between an effective diagnostic component and an ineffective diagnostic component. Therefore, as long as the object can be realized, the correction coefficient of the effective diagnostic component is not necessarily 1. For example, the correction coefficient of the effective diagnostic component may also be set to a predetermined value exceeding 1 in order to raise the contrast between the effective diagnostic component and the ineffective diagnostic component.

(3) In the above embodiment, the case of executing the ineffective diagnostic component reduction processing on two-dimensional ultrasonic image data has been described as an example. However, the ineffective diagnostic component reduction processing is not limited to the two-dimensional image data. For example, the ineffective diagnostic component reduction processing may also be executed on three-dimensional image data by dividing the three-dimensional image data into two-dimensional image data items and executing the ineffective diagnostic component reduction processing on each of the two-dimensional image data items. In addition, the ineffective diagnostic component reduction processing may also be realized by setting a small region as regions of 3×3×3=27 pixels, generating low-resolution image volume data, setting a small region (for example, a small region of 3×3=9 pixels) with a predetermined size on the image data, and performing the same processing in the unit of volume data in step S3, for example.

(4) If a predetermined maximum brightness value does not change more than a designated brightness value in observing an ultrasonic image, it is general that a visual change is not felt even if image data is updated. Accordingly, in the above embodiment, in the case when corresponding pixel values between adjacent frames, for example, before and after ineffective diagnostic component reduction processing are compared with each other and the difference is smaller than a predetermined value for all pixels, image data of a new frame of the time may not be transmitted for subsequent processing. According to such configuration, since the amount of data to be processed can be reduced, an image can be provided in real time.

In addition, various kinds of inventions may be realized by proper combination of the plurality of constituent components disclosed in the embodiments described above. For example, some constituent components may be eliminated from all components shown in the above embodiment. Moreover, constituent components in different embodiments may be appropriately combined.

What is claimed is:

1. An ultrasonic diagnostic apparatus comprising:
a data generating unit that transmits an ultrasonic wave to a predetermined region of a tested body and generates first ultrasonic image data on the basis of a reflected wave from the tested body;
a determination unit that generates second ultrasonic image data, the resolution of which is lower than that of the first ultrasonic image data, using the first ultrasonic image data and determines an effective diagnostic component and an ineffective diagnostic component on the basis of the second ultrasonic image data;
a coefficient deciding unit that decides correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and
a multiplication unit that executes image correction processing by multiplying the ineffective diagnostic component and the effective diagnostic component of the first ultrasonic image data by the correction coefficients.

2. The ultrasonic diagnostic apparatus according to claim 1,
wherein the coefficient deciding unit decides the correction coefficients as a value equal to or larger than 1 for a signal value or a pixel value at each position within the effective diagnostic component.

3. The ultrasonic diagnostic apparatus according to claim 1,
wherein the coefficient deciding unit decides the correction coefficients as a value smaller than 1 for a signal value or a pixel value at each position within the ineffective diagnostic component.

4. The ultrasonic diagnostic apparatus according to claim 1,
wherein the coefficient deciding unit decides the correction coefficients on the basis of predetermined calculation expression or a correspondence table stored beforehand.

5. The ultrasonic diagnostic apparatus according to claim 1, further comprising:
a writing unit that determines a direction of the first ultrasonic image data when written into a memory on the basis of size and shape of the predetermined region, to which an ultrasonic wave is transmitted, such that an amount of data read becomes minimal and that writes the first ultrasonic image data into the memory according to the determined direction,
wherein each of the determination unit, the coefficient deciding unit, and the multiplication unit executes processing by using the first ultrasonic image data written into the memory according to the determined direction.

6. The ultrasonic diagnostic apparatus according to claim 1,
wherein the first and second ultrasonic image data is three-dimensional image data.

7. An ultrasonic image processing apparatus comprising:
a storage unit that transmits an ultrasonic wave to a predetermined region of a tested body and stores first ultrasonic image data generated on the basis of a reflected wave from the tested body;
a determination unit that generates second ultrasonic image data, the resolution of which is lower than that of the first ultrasonic image data, using the first ultrasonic image data and determines an effective diagnostic component and an ineffective diagnostic component on the basis of the second ultrasonic image data;

a coefficient deciding unit that decides correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and a multiplication unit that executes image correction processing by multiplying the ineffective diagnostic component and the effective diagnostic component of the first ultrasonic image data by the correction coefficients.

8. The ultrasonic image processing apparatus according to claim 7, wherein the coefficient deciding unit decides the correction coefficients as a value equal to or larger than 1 for a signal value or a pixel value at each position within the effective diagnostic component.

9. The ultrasonic image processing apparatus according to claim 7,
wherein the coefficient deciding unit decides the correction coefficients as a value smaller than 1 for a signal value or a pixel value at each position within the ineffective diagnostic component.

10. The ultrasonic image processing apparatus according to claim 7,
wherein the coefficient deciding unit decides the correction coefficients on the basis of predetermined calculation expression or a correspondence table stored beforehand.

11. The ultrasonic image processing apparatus according to claim 7, further comprising:
a writing unit that determines a direction of the first ultrasonic image data when written into a memory on the basis of size and shape of the predetermined region, to which an ultrasonic wave is transmitted, such that an amount of data read becomes minimal and that writes the first ultrasonic image data into the memory according to the determined direction,
wherein each of the determination unit, the coefficient deciding unit, and the multiplication unit executes processing by using the first ultrasonic image data written into the memory according to the determined direction.

12. The ultrasonic image processing apparatus according to claim 7,
wherein the first and second ultrasonic image data is three-dimensional image data.

13. An ultrasonic image processing method comprising:
transmitting an ultrasonic wave to a predetermined region of a tested body to generate first ultrasonic image data on the basis of a reflected wave from the tested body, and generating second ultrasonic image data, the resolution of which is lower than that of the first ultrasonic image data, using the first ultrasonic image data;

determining an effective diagnostic component and an ineffective diagnostic component on the basis of the second ultrasonic image data;

deciding correction coefficients of the ineffective diagnostic component and the effective diagnostic component of the first ultrasonic image data such that a signal value or pixel value of the effective diagnostic component is relatively emphasized compared with a signal value or pixel value of the ineffective diagnostic component; and executing image correction processing by multiplying the ineffective diagnostic component and the effective diagnostic component of the first ultrasonic image data by the correction coefficients.

14. The ultrasonic image processing method according to claim 13,
wherein in the coefficient decision, the correction coefficients is decided as a value equal to or larger than 1 for a signal value or a pixel value at each position within the effective diagnostic component.

15. The ultrasonic image processing method according to claim 13,
wherein in the coefficient decision, the correction coefficients is decided as a value smaller than 1 for a signal value or a pixel value at each position within the effective diagnostic component.

16. The ultrasonic image processing method according to claim 13,
wherein in the coefficient decision, the correction coefficients are decided on the basis of predetermined calculation expression or a correspondence table stored beforehand.

17. The ultrasonic image processing method according to claim 13, further comprising:
determining a direction of the first ultrasonic image data when written into a memory on the basis of size and shape of the predetermined region, to which an ultrasonic wave is transmitted, such that an amount of data read becomes minimal and writing the first ultrasonic image data into the memory according to the determined direction,
wherein in each of the determination of the effective diagnostic component and the ineffective diagnostic component, the coefficient decision, and the multiplication, processing is executed by using the first ultrasonic image data written into the memory according to the determined direction.

18. The ultrasonic image processing method according to claim 13,
wherein the first and second ultrasonic image data is three-dimensional image data.

* * * * *

UNITED STATES PATENT AND TRADEMARK OFFICE
CERTIFICATE OF CORRECTION

| | | |
|---|---|---|
| PATENT NO. | : 8,216,145 B2 | Page 1 of 1 |
| APPLICATION NO. | : 12/338101 | |
| DATED | : July 10, 2012 | |
| INVENTOR(S) | : Tomohisa Imamura et al. | |

It is certified that error appears in the above-identified patent and that said Letters Patent is hereby corrected as shown below:

On the title page, Item (54) and column 1 should read:

--(54)  ULTRASONIC DIAGNOSTIC APPARATUS, ULTRASONIC IMAGE PROCESSING APPARATUS, AND ULTRASONIC IMAGE PROCESSING METHOD--

Signed and Sealed this
Eighteenth Day of September, 2012

David J. Kappos
*Director of the United States Patent and Trademark Office*